United States Patent
Schwartz et al.

(10) Patent No.: US 9,470,697 B2
(45) Date of Patent: Oct. 18, 2016

(54) METHODS FOR DETECTING RISK OF FATAL PROSTATE CANCER USING SERUM CALCIUM

(71) Applicant: Wake Forest University Health Sciences, Winston-Salem, NC (US)

(72) Inventors: Gary G. Schwartz, Winston-Salem, NC (US); Halcyon G. Skinner, Middleton, WI (US)

(73) Assignee: Wake Forest University Health Services, Winston-Salem, NC (US)

( * ) Notice: Subject to any disclaimer, the term of this patent is extended or adjusted under 35 U.S.C. 154(b) by 218 days.

(21) Appl. No.: 14/495,260

(22) Filed: Sep. 24, 2014

(65) Prior Publication Data

US 2015/0010934 A1 Jan. 8, 2015

Related U.S. Application Data

(62) Division of application No. 12/644,209, filed on Dec. 22, 2009, now Pat. No. 8,871,458.

(60) Provisional application No. 61/141,068, filed on Dec. 29, 2008.

(51) Int. Cl.
| | |
|---|---|
| *G01N 33/84* | (2006.01) |
| *G01N 27/00* | (2006.01) |
| *G01N 33/574* | (2006.01) |
| *G01J 3/42* | (2006.01) |
| *G01J 3/46* | (2006.01) |

(52) U.S. Cl.
CPC .............. *G01N 33/84* (2013.01); *G01N 27/00* (2013.01); *G01N 33/57434* (2013.01); *G01J 3/42* (2013.01); *G01J 3/46* (2013.01); *G01N 33/574* (2013.01)

(58) Field of Classification Search
CPC .................................. G01J 3/42; G01N 33/84
See application file for complete search history.

(56) References Cited

U.S. PATENT DOCUMENTS

| 6,383,817 B2 | 5/2002 | Schwartz |
| 2004/0087559 A1 | 5/2004 | Schwartz et al. |

OTHER PUBLICATIONS

Chan JM et al. Dairy products, calcium, and prostate cancer risk in the Physicians Health Study. American Journal of Clinical Nutrition. 2001; 74: 549-554.
Giovannucci E et al. A prospective study of calcium intake and incident and fatal prostate cancer. Cancer Epidemiology Biomarkers preview. 2006; 15: 203-210.
Weaver CM. Assessing calcium status and metabolism. Journal of Nutrition. 1990; 120: 1470-1473.
Pelger RCM et al. Effects of the bisphosphonate olpadronate in patients with carcinoma of the prostate metastatic to the skeleton. Bone. Apr. 1998; 22(4): 403-408.
Drop LJ et al. Determination of blood ionized calcium in a large segment of the normal adult population. Clinica Chimica Acta, 1978; 89: 503-510.
Bowers GN et al. Measurement of ionized calcium in serum with ion-selective electrodes: a mature technology that can meet the daily service needs. Clin Chem. 1986; 32(8): 1437-1447.
Henry JB. Analytical Techniques, Clinical Diagnosis and Management by Laboratory Methods, 12 ed. Ch. 10. (2001) 195-196.
Sava L et al. Serum calcium measurement : total versus free (ionized) calcium. Indian Journal of Clinical Biochemistry. 2005; 20(2): 158-161.
Sugano M et al. New enzymatic assay using phospholipase D to measure total calcium in serum. Clinical Chemistry. 2005; 51(6): 1021-1024.
Calvi LM and Businsky DA, When is it appropriate to order an ionized calcium? J Am Soc Nephrol. 2008; 19: 1257-1260.
Skinner HG and Schwartz GG. Serum calcium and incident and fatal prostate cancer in the national health and nutrition examination survey. Cancer Epidemiol Biomarkers Prev. 2008; 17(9): 2302-2305.
Agrawal S and Dunsmuir WD, Molecular markers in prostate cancer. Part 1: predicting lethality, Asian Journal of Andrology, 2009; 11: 14-21.
Al Zharani A and Levine MA. Primary hyperparathyroidism. Lancet. Apr. 26, 1997; 349: 1233-38.
Phang JM et al. Dietary perturbation of calcium metabolism in normal man: compartmental analysis. The Journal of Clinical Investigation, Jan. 1969; 48(1): 67-77.
Kemm JR. The effect of previous dietary intake of calcium on calcium absorption in rats, J Physiol. Jun. 1972; 223: 321-332.
Nordin BE. Calcium homeostasis. Clinical Biochemistry, Feb. 1994; 23: 3-10.
Kurokawa K. How is plasma calcium held constant? *Milieu interieur* of calcium. Kidney International. 1996; 49: 1760-1764.
Mundy GR and Guise TA. Hormonal control of calcium homeostasis. Clinical Chemistry. 1999; 45:8(B): 1347-1352.
Jorde R et al. Determinants of serum calcium in men and women, The Tromsø study, European Journal of Epidemiology. 2001; 17(12); 1117-1123.
Drake MT et al. Bisphosphonates; mechanism of action and role in clinical practice. Mayo Clinic Proceedings. Sep. 2008; 83(9): 1032-1045.
Schwartz GG. Vitamin D, sunlight, and the epidemiology of prostate cancer. Anti-Cancer Agents in Medicinal Chemistry, 2013; 13(1): 45-57.
Hanchette CL and Schwartz GA Geographic patterns of prostate cancer mortality: evidence for a protective effect of ultraviolet radiation. Cancer, Dec. 15, 1992; 70(12): 2861-2869.

(Continued)

*Primary Examiner* — Renee Claytor
*Assistant Examiner* — Tiffany Gough
(74) *Attorney, Agent, or Firm* — Myers Bigel & Sibley, P.A.

(57) ABSTRACT

A method of screening for increased risk of fatal prostate cancer in a subject comprises providing a blood sample collected from the subject, and then detecting the presence or absence of an increased level of serum calcium in the sample. An increased level of serum calcium indicates the subject is at increased risk of fatal prostate cancer.

5 Claims, No Drawings

(56) References Cited

OTHER PUBLICATIONS

Schwartz GG. Vitamin D and intervention trials in prostate cancer: from theory to therapy. Annals of Epidemiology, Feb. 2009; 19(2): 96-102.

Schwartz GG and Hulka BS. Is vitamin D deficiency a risk factor for prostate cancer? (hypothesis). Anticancer Research, 1990; 10(5A): 1307-1311.

Schwartz GG. Vitamin D and the epidemiology of prostate cancer. Seminars in Dialysis. Jul.-Aug. 2005; 18(4): 276-289.

Schwartz GG. Circulating vitamin D and risk of prostate cancer-letter. Cancer Epidemiology, Biomarkers & Prevention. Jan. 2012; 21(1): 246.

Tseng M et al. Dairy intake and 1,25-dihydroxyvitamin D levels in men at high risk for prostate cancer, Cancer Causes Control, 2009; 20: 1947-1954.

Schwartz GG. Is serum calcium a biomarker of fatal prostate cancer? Future Oncol. 2009; 5(5): 577-580.

Siyam FF and Klachko DM. What is hypercalcemia? The importance of fasting samples, CardioRenal Medicine, 2013; 3: 232-238.

Schwartz GG. Advanced prostate cancer lowers serum calcium levels-Implications for epidemiologic studies, Nutrition and Cancer, 2014; 66(3): 531-532.

METHODS FOR DETECTING RISK OF FATAL PROSTATE CANCER USING SERUM CALCIUM

RELATED APPLICATIONS

The present application is a divisional of and claims priority to U.S. patent application Ser. No. 12/644,209, filed Dec. 22, 2009, now allowed, which claims the benefit of U.S. Provisional Patent Application Ser. No. 61/141,068, filed Dec. 29, 2008, the disclosure of each of which is incorporated by reference herein in its entirety.

GOVERNMENT SUPPORT

This invention was made with US Government Support under grant number CA 014520 from the National Institutes of Health. The U.S. Government has certain rights to this invention.

FIELD OF THE INVENTION

The present invention concerns methods of detecting or screening for risk of fatal prostate cancer.

BACKGROUND OF THE INVENTION

Prostate cancer is the second most fatal cancer among men in the United States, accounting for approximately 28,000 deaths in 2008 (American Cancer Society. Cancer Facts and Figures 2008. Atlanta: American Cancer Society; 2008 2008). Considerable epidemiologic attention in prostate cancer has focused on the vitamin D-endocrine system and on calcium (Schwartz G G. Vitamin D and the epidemiology of prostate cancer. Semin Dial 2005; 18:276-89; Ahn J, Peters U, Albanes D, et al. Serum vitamin D concentration and prostate cancer risk: a nested case-control study. J Natl Cancer Inst 2008; 100:796-804; Tseng M. et al., Dairy, calcium, and vitamin D intakes and prostate cancer risk in the National Health and Nutrition Examination Epidemiologic Follow-up Study cohort. Am J Clin Nutr 2005; 81:1147-54). Although numerous studies have investigated prostate cancer with respect to calcium intake from the diet, the subject of calcium in serum has received scarce attention, perhaps because calcium levels in serum are believed to be under strict homeostatic control. In the only study to specifically address this question, we found an approximately 3-fold increased risk of fatal prostate cancer in the National Health and Nutrition Examination Survey (NHANES I) Epidemiologic Follow Study (NHEFS) for men with total serum levels of calcium in the upper tertile at the baseline exam (Skinner H G, Schwartz G G. Serum calcium and incident and fatal prostate cancer in the National Health and Nutrition Examination Survey. Cancer Epidemiol Biomarkers Prev 2008; 17:2302-5).

SUMMARY OF THE INVENTION

A first aspect of the invention is, accordingly, a method of screening for increased risk of fatal prostate cancer in a human male subject, comprising: providing a blood sample collected from said subject; and then detecting (and preferably quantitatively detecting) the presence or absence of an increased level of serum calcium in said sample (e.g., as compared to subjects not at increased risk of fatal prostate cancer; e.g., detecting a serum calcium level in the top tertile, or the top or middle tertile, of serum calcium levels for a representative population of human male subjects)), an increased level of serum calcium indicating said subject is at increased risk of fatal prostate cancer.

In some embodiments, the serum calcium detected is total serum calcium; in other embodiments, the serum calcium detected is ionized serum calcium.

For example, when the serum calcium detected is total serum calcium, the detecting step preferably comprises detecting a total serum calcium level greater than 2.3 or 2.4 mmol/L, to thereby provide an indication of increased risk of fatal prostate cancer in the subject.

In another example, when the serum calcium is ionized serum calcium, the detecting step preferably comprises detecting an ionized serum calcium level greater than 1.2 (or more particularly 1.22) or 1.3 (or more particularly 1.26) mmol/L to provide an indication of increased risk of fatal prostate cancer in the subject.

A further aspect of the present invention is the use of a means for detecting blood or serum calcium levels for carrying out a method of screening for increased risk of fatal prostate cancer in a human male subject, such as a method described herein below.

DETAILED DESCRIPTION OF THE PREFERRED EMBODIMENTS

Subjects on which the invention may be carried out are, in general, human male subjects, are typically adult subjects (e.g., greater than 18 or 21 years of age), in some embodiments are at least 40 years old, and in some embodiments are geriatric subjects (e.g., greater than 65 or 70 years old).

Blood samples can be collected from subjects by any suitable means, including but not limited to finger stick, venipuncture/phlebotomy, etc. Typically the blood sample is whole blood as it is withdrawn or collected from the subject, which is then at least partially purified (e.g., to produce blood plasma or blood sample) to produce the blood sample on which the detecting step is carried out.

The detecting step or procedure can be carried out in accordance with known techniques, or variations thereof that will be apparent to those skilled in the art, In general, the detecting step is a quantitative detecting step. Suitable detecting procedures include, but are not limited to, absorption spectrometry (e.g., infrared absorption spectrometry, atomic absorption spectrometry), detection with an ion (and specifically calcium) selective electrode, colorimetric detection, fluorescent detection, enzymatic detection, etc. See generally J. Henry, Clinical Diagnosis and Management by Laboratory Methods, Chap. 10, pgs. 195-196 ($20^{th}$ Ed. 2001), Ion selective electrodes. Ionized serum calcium can be detected with an ion-selective electrode in accordance with known techniques, or variations thereof that will be apparent to those skilled in the art. See, e.g., L. Sava et al., *Indian Journal of Clinical Biochemistry* 20(2), 158-161 (2005); G. Bowers et al., *Clin. Chem.* 32/8, 1437-1447 (1986). In general, such methods involve contacting the sample to an ion-selective electrode; and then measuring (e.g., potentiometrically) ionized calcium in the sample through the electrode.

Atomic absorption spectrophotometry. This method can, in general, be carried out by atomizing (e.g., by a flame or heat) the sample in an atomic absorption spectrophotometer to provide an atomized sample; then illuminating the atomized sample with light (e.g., laser light) in the spectrophotometer; then detecting light from said atomized sample with a detector; and then determining the amount of total serum calcium in said sample from said detected light by atomic absorption spectrophotometry. Samples may be diluted with lanthanum HCl to reduce viscosity and interference, and Strontium may be added or included as an internal standard to correct for fluctuations in the flame and atomization rate. J. Henry, *Supra* at 196.

Colorimetric analysis. Total serum calcium can be colorimetrically analyzed by, for example, combining the sample with a metallochromic indicator dye that binds calcium to form a complex (e.g., arsenazo dye or orthocresolphthalein complexone); and then colorimetrically measuring the formation of the complex (e.g., with a colorimeter or spectrophotometer) to determine the amount of calcium in said sample. J. Henry, *Supra*. at 195.

Fluorescent analysis. Total serum calcium can be fluorescently analyzed by, for example, combining said sample with a chelating agent (e.g., EDTA, EGTA) that binds calcium and forms a fluorescent complex therewith; and then detecting fluorescence from said sample to determine the amount of calcium in said sample. J. Henry, *Supra*. at 195.

Enzymatic assay. Total serum calcium can be enzymatically determined by, for example, combining the sample with an enzyme that is either activated or inhibited by calcium, and then detecting the activation or inhibition of said enzyme to determine the amount of calcium in said sample. See, e.g., M. Sugano, *Clinical Chemistry* 51, 1021-1024 (2005). Suitable enzymes include, but are not limited to, alpha amylase, phospholipase D, or urea amidolyase.

Utility. We show here that a man with a total serum calcium in the upper tertile of the normal distribution is approximately 3 times more likely to develop fatal prostate cancer and that a man with an ionized serum calcium in the upper tertile of the normal distribution is >3 times more likely to develop fatal prostate cancer We envision that the greatest use of tests such as the ionized calcium test will be to give quantitative information to men about their probability of having a fatal form of prostate cancer, given a histological diagnosis of prostate cancer. Men need this information because it would help to inform their decisions about whether to get definitive therapy (e.g., surgery or radiation therapy) for their cancer. This is a life-altering decision.

Based on the two most recent years of available data from the United States' SEER (Surveillance Epidemiology and End Results) Program, the case-fatality rate from prostate cancer (the proportion of men who die from prostate cancer following a diagnosis of prostate cancer) is 17.5% or roughly 1 in 6. In other words, of 6 men who today receive a diagnosis of prostate cancer, if none were treated, only 1 of the 6 would die of his prostate cancer. (The others would die from causes unrelated to their prostate cancer, e.g., heart disease.) Conversely, if all 6 were treated, 5 of the 6 would be treated unnecessarily and at considerable cost to their quality of life as treatment causes impotence in virtually all men, urinary and bowel incontinence (at least temporary) of a few percent, and death in about 1% of men who elect surgery.

Using the results described herein, we can compute the case-fatality rates from prostate cancer within tertiles of total or ionized serum calcium by weighting the prognosis in each tertile according to the relative risks we observed.

$\frac{1}{3}(x)+\frac{1}{3}(1.8)(x)+\frac{1}{3}(3.1)x=0.175$. This yields the following case-fatality rates by tertile of ionized calcium:

0.089, 0.160, 0.276

These correspond to the following lifetime probabilities of death in each tertile of ionized calcium: $\frac{1}{11}$ for the lowest tertile, $\frac{1}{6}$ for the middle tertile, and $\frac{1}{4}$ for the highest tertile.

Thus, the information that an ionized calcium test result could provide to men (who without the test result all start with a risk of fatal prostate cancer of 1 in 6) is that their risk is actually 50% greater than 1 in 6 (i.e., 1 in 4) or more than 50% lower than 1 in 6, 1 in 11, Because the decision to have definitive therapy is irrevocable once acted upon and is life-altering, we believe that many men would want personalized, numerical guidance about their probability of having cancer that is likely to be fatal and therefore cancer that requires treatment. For example, many men might be inclined to defer therapy if they learned that their risk of fatal disease was approximately 1 in 11.

Before a diagnosis of prostate cancer has been made. An important feature of our discovery is that the prognostic value of the test precedes the diagnosis of prostate cancer. Because of this, we are able to stratify men into risk categories years before a prostate cancer occurs. Men in the highest risk group may opt to have more intensive screening, or to begin screening at an earlier age (as is done for black men, or men with a family history of early prostate cancer). Men in the lowest risk group may opt to delay or to forego screening, potentially saving themselves from the consequences of over-diagnosis and/or unnecessary treatment (for example, impotence and incontinence).

Comparison with breast cancer. In determining the utility of our technology for predicting fatal prostate cancer, it may be helpful to compare it to an analogous technology. Mutations in the BRCA1 gene are associated with a roughly three-fold increased risk for breast cancer in women. This association is similar in magnitude to the association we observe between ionized serum calcium and fatal prostate cancer. Note that this risk is for a diagnosis of breast cancer NOT for prediction of the fatality of the disease (unlike our technology).

Although BRCA1 mutation is relatively rare, many women pay several hundred to several thousand dollars to learn their BRCA1 status. In the group with the highest prevalence of BRCA1 mutations, women of Ashekenazi ancestry, the prevalence of BRCA1 mutations ranges from 7% in women with no family history of early breast or ovarian cancer to 28% in women with a family history of early breast and ovarian cancer. This can be compared to 33.3% of men who fall in to the highest textile of serum calcium, The importance of the information provided by this level of risk (a three-fold increase) can be measured by the choices women make when they test positive for the mutation, Some opt for increased surveillance by mammography, some opt for chemopreventive strategies, and some opt for prophylactic surgery to remove the breasts and/or ovaries.

The present invention is explained in greater detail in the following non-limiting Examples.

EXAMPLE 1

METHODS. We conducted a prospective cohort study of total serum calcium and risk for incident and fatal prostate cancer using the first National Health and Nutrition Examination Survey (NHANES) and the NHANES Epidemiologic Follow-up Study (National Center for Health Statistics. Plan and operation of the NHANES I Epidemiologic Follow-up Study, 1992. Washington, D.C.: DHHS, 1997; National Center for Health Statistics. Plan and operation of the NHANES I Epidemiologic Follow-up Study, 1987. Washington, D.C.: DHHS, 1992; National Center for Health Statistics. Plan and operation of the HANES 1 Augmentation Survey of Adults 25-74 years, United States, 1974-75. Washington, D.C.: DHHS, 1978; National Center for Health Statistics, Plan and operation of the Health and Nutrition Examination Survey, United Slates, 1971-73. Washington, D.C.: DHEW, 1973). We included males aged 24 to 77 years at baseline examination in 1971-1975. Participants who reported lung, colon, or prostate cancers prior to the baseline exam (n=102) and those who reported prostate cancer or died within one year of baseline (n=90) were excluded. The final analytical cohort included 2,814 men for whom baseline serum calcium measurements were available.

Person-time at risk was calculated as the interval between the dates of initial examination and prostate cancer diagnosis or death (for cases) or date of last contact (for non-cases). Prostate cancer was ascertained by self-report (with or without a recorded hospital stay) and by death certificate. Cases with a death record were considered fatal cases, and all others were considered non-fatal cases. For cases with a hospital record, the date of diagnosis was the date of first admission for prostate cancer. For cases without hospital record the diagnosis date was defined as June 30 of the year of self-report. For cases confirmed by death certificate only, the date of diagnosis was the date of death, The earliest diagnosis date was used for cases with multiple dates. Fatal cases were identified through death record linkage with 'prostate cancer' mentioned as a cause of death.

RESULTS. Eighty-five incident cases of prostate cancer, including 25 fatal cases, were observed among 2,814 men over 46,188 person-years of follow-up (1971-1993). The 25 fatal cases included 10 cases for which the death certificate was the only record of prostate cancer. Men with higher serum calcium tended to be younger (46 versus 52 years in the $3^{rd}$ and $1^{st}$ tertiles respectively), and were more likely to be black (15.4% versus 11.6% black in the $3^{rd}$ and $1^{st}$ tertiles). There was no evidence of increased risk of incident disease with increasing serum calcium levels. Conversely, comparing men in the top to men in the bottom tertile of serum calcium, we observed a significantly increased hazard for fatal prostate cancer that persisted after adjustment for age (age-adjusted relative hazard of 2.59 (95% Confidence Interval, 1.00-6.72; $P_{trend}$=0.05), BMI (age- and BMI-adjusted relative hazard=2.62, Confidence Interval 1.01-6,80; $P_{trend}$=0.04) and race (age- and BMI- and race-adjusted relative hazard=2.68 (95% Confidence Interval 1.02-6.99; $P_{trend}$=0.04). Tests for linear trend were statistically significant. However, most of the excess risk was concentrated in the top tertile of serum calcium. There was no substantive difference between adjusting for BMI as a continuous or categorical variable. Adjustment for family history of prostate cancer did not alter the point estimate but widened the confidence interval ($P_{trend}$=0.06). We did not detect statistically significant interactions between serum calcium and other major risk factors for prostate cancer, but power was limited.

TABLE 1

Selected baseline characteristics of men in the National Epidemiologic Follow-up Study to the first National Health and Nutrition Examination Survey by tertile of serum calcium.

| | Serum Calcium | | |
| --- | --- | --- | --- |
| | Tertile 1 | Tertile 2 | Tertile 3 |
| Mean calcium (mg/dl) ± SD | 9.3 ± 0.3 | 9.7 ± 0.1 | 10.2 ± 0.3 |
| Number of participants | 992 | 807 | 1012 |
| Age (years) | 52.2 | 48.3 | 45.5 |
| Body mass index (kg /m$^2$) | 25.9 | 25.8 | 25.7 |
| Race (% Black) | 11.6 | 9.7 | 15.4 |
| Family history of prostate cancer (%) | 0.9 | 1.3 | 1.3 |

TABLE 2

Relative hazards* for incident and fatal prostate cancer by tertile of serum calcium in the National Health and Nutrition Examination Survey's Epidemiologic Follow-up Study.

| | Tertile of serum calcium (Median value) | | | |
| --- | --- | --- | --- | --- |
| | Tertile 1 (9.3 mg/dl) | Tertile 2 (9.7 mg/dl) | Tertile 3 (10.1 mg/dl) | P-trend |
| Prostate cancer incidence | | | | |
| Number of incident cases | 34 | 22 | 29 | |
| Person-years at risk | 15556 | 13712 | 16920 | |
| Age-adjusted Relative Hazards | 1.00 (Reference) | 0.93 (0.54-1.60) | 1.25 (0.76-2.07) | 0.409 |
| +BMI | 1.00 (Reference) | 0.93 (0.54-1.60) | 1.25 (0.76-2.07) | 0.404 |
| +Race | 1.00 (Reference) | 0.93 (0.54-1.59) | 1.29 (0.78-2.13) | 0.361 |
| +Family history | 1.00 (Reference) | 0.97 (0.56-1.70) | 1.31 (0.77-2.20) | 0.341 |
| Prostate cancer mortality | | | | |
| Number of fatal cases | 7 | 7 | 11 | |
| Person-years at risk | 15556 | 13712 | 16920 | |
| Age-adjusted Relative Hazards | 1.00 (Reference) | 1.64 (0.57-4.71) | 2.59 (1.00-6.72) | 0.049 |
| +BMI | 1.00 (Reference) | 1.66 (0.58-4.74) | 2.62 (1.01-6.80) | 0.046 |
| +Race | 1.00 (Reference) | 1.65 (0.58-4.72) | 2.68 (1.02-6.99) | 0.043 |
| +Family history | 1.00 (Reference) | 1.72 (0.55-5.37) | 2.68 (0.94-7.64) | 0.063 |

*Each model is adjusted for the listed variable and all prior variables.

In summary, in this prospective cohort, we observed an approximately 3-fold increased risk for fatal prostate cancer among men in the upper tertile of the distribution of total serum calcium. We observed a significant dose-response. To our knowledge, this is the first study to examine prostate cancer risk in relation to serum calcium. The measurement of serum calcium preceded the diagnosis of prostate cancer by an average of 9.9 years (SD=4.5 years).

EXAMPLE 2

In this example we confirm and extend the finding of Example I using an independent cohort, NHANES III A unique feature of NHANES III is that it included measurements of ionized serum calcium, the physiologically active fraction of total serum calcium.

METHODS. Data were derived the Third National Health and Nutrition Examination Survey (NHANES III), which provides public-use mortality files with record linkage of participants in NHANES III to the National Death Index (National Center for Health Statistics (U.S.), Plan and operation of the third National Health and Nutrition Examination Survey, 1988-94. Hyattsville, Md. Washington, D.C.: U.S. Dept. of Health and Human Services, Public Health Service, Centers for Disease Control and Prevention; 1994). Eight thousand one hundred twenty-five (8,125) men participated in NHANES III. We excluded men with missing information on serum calcium (n=1,210); a prior history of cancer (except non-melanoma skin cancer) (n=199); men who died from prostate cancer within 12 months of examination (n=2), and men without follow-up information (n=4). The final analytical cohort consisted of 6,710 men aged 18-90 years at the baseline examination in 1988-1994, Because of the concern that calcium levels in serum could be influenced by the presence of undetected prostate cancer, we performed additional analyses excluding prostate cancer deaths that occurred during the first three years of follow up (N=8 deaths).

We evaluated associations between prostate cancer mortality, total serum calcium and ionized serum calcium corrected for serum pH. Approximately half of the total serum calcium is in the ionized or physiologically active state. Another 40% is bound to serum proteins, principally albumin, and the remaining 10% is bound to anions such as lactate and phosphate. Because the binding of calcium to proteins is altered by changes in blood pH, measures of ionized calcium in blood commonly are pH-corrected to a standard pH using regression analysis (Dickerson R N, et al., Accuracy of methods to estimate ionized and "corrected" serum calcium concentrations in critically ill multiple trauma patients receiving specialized nutrition support. JPEN J Parenter Enteral Nutr 2004; 28:133-41).

Person-time was computed as the number of months from initial examination to date of prostate cancer mortality (events), death from another cause, or the end of follow-up in Dec. 31, 2000 (non-events). We estimated relative risks adjusted for potential confounders using Cox proportional hazards. Multivariate models included age (in one-year increments), body mass index (BMI; as a continuous measure), as potential confounders, and variables related to NHANES III sample weights (race/ethnicity (black/white and Hispanic/non-), household size (number of individuals up to 10), and general health status (Excellent, Very Good, Good, Fair, Poor) to account for differential probabilities of selection and non-response (Korn E L, Graubard B I. Epidemiologic studies utilizing surveys: accounting for the sampling design. Am J Public Health 1991; 81:1166-73), Statistical analysis employed SAS (v9.1 for Linux) and Sudaan (v9 for Linux) to account for the complex sampling designs of the cohort. All statistical tests were two-sided.

RESULTS. Twenty five prostate cancer deaths occurred among 6,710 men over 56,625 person-years of follow-up. Measurement of serum calcium preceded fatal prostate cancer by an average of 5.3 years (SD=2.5), The prostate cancer cases' average age at baseline was 73.4 years and their average age at death was 78.1 years. Men in the higher tertiles of total serum calcium tended to be younger, to be black, to have lower BMI, to be from a large household, and to be in good or better health. Similar relationships were observed for increasing tertiles of ionized calcium. The mean ages in tertiles one through three were 45.2, 41.4, and 38.5 years respectively.

Compared to men in the lowest tertile of total serum calcium, men in the highest tertile had a multivariate-adjusted relative risk for prostate cancer death of 2.07 (95% Confidence Interval, C.I.: 1.06-4.04). This association was not materially changed after adjustment for BMI (RR=2.02; 95% C.I. 1.02-4.01). The relative risk for men in the second tertile was 1.39 (95% C.I. 0.59-3.30). The test for linear trend was not statistically significant ($P_{trend}$=0.26). Compared to men in the lowest tertile of ionized serum calcium, the relative risk for fatal prostate cancer among men in the highest tertile was 3.18 (95% C.I. 1.09-9.28). Adjustment for BMI did not substantially alter this risk (RR=3.12; 95% C.I. 1.04-9.43). The relative risk for men in the second tertile was 1.82 (95% C.I. 0.64-5.12). The linear trend was not statistically significant ($P_{trend}$=0.15).

TABLE 3

Selected baseline characteristics of men in the Third National Health and Nutrition Examination Survey (NHANES III). 1988-1994.*

|  | Total Serum Calcium | | |
| --- | --- | --- | --- |
|  | Tertile 1 | Tertile 2 | Tertile 3 |
| Number of participants | 2,205 | 2,131 | 2,374 |
| Weighted population | 22,801,773 | 23,404,681 | 27,861,959 |
| Mean total calcium (mmol/L) | 2.20 | 2.32 | 2.42 |
| Mean ionized calcium (mmol/L) | 1.20 | 1.24 | 1.27 |
| Age (years) | 47.7 | 43.1 | 38.3 |
| Body mass index (kg/m$^2$) | 26.7 | 26.9 | 26.1 |
| Race (% Black) | 8.0 | 10.3 | 11.4 |
| Large household (% with 5 or more people) | 36.6 | 41.9 | 45.6 |
| Health (% Good or better) | 91.2 | 93.4 | 95.0 |

*Means and proportions in this table account for the complex sample design and differential probabilites of non-response in NHANES III and are representative of the total population of U.S. men.

NOTE:

To convert total calcium or ionized calcium from mmol/L to mg/dL, divide mmol/L by 0.2495

In summary, we found a doubling of risk for fatal prostate cancer among men in the highest tertile of total serum calcium and a tripling of risk for men in the highest tertile of ionized serum calcium. The results for total serum calcium are consistent with our findings for prostate cancer mortality in NHANES I in which we observed a multi-variable adjusted RR of 2.68. This is the first study to examine prostate cancer risk in relation to prediagnostic levels of ionized serum calcium.

TABLE 4

Relative hazards* for prostate cancer mortality by tertiles of total and ionized serum calcium in the Third National Health and Nutrition Examination Survey (NHANES III)

|  | Tertile of serum calcium | | | |
|---|---|---|---|---|
|  | Tertile 1 | Tertile 2 | Tertile 3 | P-trend |
| Total Serum Calcium (mmol/L) | | | | |
| Median (Range) mmol/L | 2.22 (1.06-2.27) | 2.31 (2.28-2.35) | 2.41 (2.36-3.06) | |
| Number of deaths | 9 | 8 | 8 | |
| Person-months at risk | 218,964 | 216,797 | 243,725 | |
| Age-adjusted Relative Hazards | 1.00 (Reference) | 1.39 (0.59-3.30) | 2.07 (1.06-4.04) | 0.258 |
| +Body Mass Index | 1.00 (Reference) | 1.36 (0.57-3.26) | 2.02 (1.02-4.01) | 0.287 |
| Ionized Serum Calcium (mmol/L) | | | | |
| Median (Range) mmol/L | 1.19 (0.99-1.21) | 1.24 (1.22-1.25) | 1.28 (1.26-1.60) | |
| Number of deaths | 6 | 8 | 11 | |
| Person-months at risk | 199,120 | 252,180 | 228,186 | |
| Age-adjusted Relative Hazards | 1.00 (Reference) | 1.82 (0.64-5.12) | 3.18 (1.09-9.28) | 0.152 |
| +Body Mass Index | 1.00 (Reference) | 1.81 (0.63-5.20) | 3.12 (1.04-9.43) | 0.160 |

*In addition to adjustement for age (one-year intervals) and body mass index (as a continuous measure), all models are adusted for variables used in NHANES III sample weighting: an interaction between senior status (age >60 years) and race/ethnicity, household size, and general health status (Excellent/VeryGood/Good/Fair/Poor). Models account for clustering of observations in complex sampling design of NHANES III. Ionized serum calcium is pH corrected.

The foregoing is illustrative of the present invention, and is not to be construed as limiting thereof. The invention is defined by the following claims, with equivalents of the claims to be included therein.

That which is claimed is:

1. A method of screening for increased risk of developing fatal prostate cancer in a human male subject in need thereof and treating said prostate cancer, comprising:
providing a blood sample collected from said subject; and
detecting the presence or absence of an increased level of ionized serum calcium in said sample by contacting said sample to an ion-selective electrode; and then potentiometrically measuring ionized calcium in said sample through said electrode, an increased level of greater than 1.2 mmol/L ionized serum calcium indicating said subject is at increased risk of developing fatal prostate cancer, and wherein upon detecting the presence of said increased level greater than 1.2 mmol/L, the method further comprises treating said prostate cancer with surgery, radiation therapy or combinations thereof.

2. The method of claim 1, wherein said blood sample comprises whole blood, blood plasma, or blood serum.

3. The method of claim 1, wherein said providing step comprises collecting a blood sample from said subject.

4. The method of claim 1, wherein said providing step comprises at least partially purifying said blood sample.

5. The method of claim 1, wherein said detecting step is a quantitative detecting step.

* * * * *